United States Patent [19]

Tavss et al.

[11] 4,451,385

[45] May 29, 1984

[54] AGENT FOR REDUCING DETERGENT IRRITATION TO SKIN AND EYES

[75] Inventors: Edward A. Tavss, Kendall Park; Edward Eigen, East Brunswick; Kenneth F. Clark, Hazlet, all of N.J.

[73] Assignee: Colgate-Palmolive Company, New York, N.Y.

[21] Appl. No.: 357,917

[22] Filed: Mar. 15, 1982

[51] Int. Cl.$^3$ .......................... C07G 7/00; C08H 1/06
[52] U.S. Cl. ................................. 252/132; 252/89.1; 252/174.23; 252/DIG. 5; 252/DIG. 13; 252/DIG. 14; 260/112 R; 260/117; 260/118; 260/123.7; 424/70; 424/359
[58] Field of Search ............... 252/DIG. 5, DIG. 13, 252/DIG. 14, 89.1, 132, 174.23; 260/112 R, 123.7, 117, 118; 424/70, 359

[56] References Cited

U.S. PATENT DOCUMENTS

| | | | |
|---|---|---|---|
| 3,548,056 | 12/1970 | Elgen et al. ......................... | 424/171 |
| 3,898,186 | 8/1975 | Mermelstein et al. .............. | 252/528 |
| 4,076,800 | 2/1978 | Marsh et al. ......................... | 424/70 |
| 4,087,518 | 5/1978 | Smith et al. ......................... | 424/70 |
| 4,115,548 | 9/1978 | Marsh et al. ......................... | 424/70 |
| 4,195,077 | 3/1980 | Marsh et al. ......................... | 424/70 |
| 4,307,013 | 12/1981 | Ohtsuka et al. ................. | 260/112 R |

FOREIGN PATENT DOCUMENTS 1478014 6/1977 United Kingdom .
1529841 10/1978 United Kingdom .

OTHER PUBLICATIONS

Ency. of Chem. Tech., vol. 11 (1953), pp. 212–213, Kirk et al.
Hackh's Chemical Dictionary, p. 689, 3rd Edition, 1944.
Sephadex ® Ion Exchangers (1973), pp. 10 & 11.
Cleaning Composition Containing Proteins Obtained by Condensation of Fatty Acids with Polypeptides, Chemical Abstract, vol. 71, p. 124, 1969.
3-of Dental Research, vol. 56, B109, Special Issue B, 1977, Vratsanos et al.
Pharmacia Brochure, 1973, Sephadex ® Ion Exchangers, pp.22–34.

Primary Examiner—Howard E. Schain
Attorney, Agent, or Firm—Richard N. Miller; Murray M. Grill; Herbert S. Sylvester

[57] ABSTRACT

A liquid detergent composition containing an anionic surfactant and a minor amount of a water-soluble, positively charged, partially hydrolyzed, protein fraction containing a high concentration of basic amino acids, having an isoionic point greater than 7 and a Bloom gel value of zero which counters the irritation caused by said anionic surfactant without reducing its foaming and detergency properties.

10 Claims, No Drawings

AGENT FOR REDUCING DETERGENT IRRITATION TO SKIN AND EYES

FIELD OF THE INVENTION

The present invention relates to novel light duty liquid detergent compositions useful as dishwashing liquids, shampoos, and the like, which are substantially non-irritating to the skin and eyes, comprising an anionic surfactant and a positively charged, water soluble, partially hydrolyzed, protein fraction containing a high concentration of basic amino acids which is obtained by extraction from a partially hydrolyzed protein mixture. Separation of proteins, based on charge, can be obtained by means of batch phase, ion exchange treatment or column ion exchange chromatography utilizing an anion exchange resin.

BACKGROUND AND PRIOR ART

Liquid detergents containing anionic surface active agents, such as dishwashing products, are known to contribute to skin damage such as chapping. Similarly, shampoos containing anionic surface active agents cause skin and eye irritation. Non-ionic surface active agents cause little or no skin and eye irritation, so they may and have been used instead. However, the non-ionics are inferior to anionic agents both in foaming power and detergency.

It has been found that the addition of a partially hydrolyzed protein fraction rich in positively charged amino acids, having an isoionic point of 7 to 11 and a Bloom gel value of zero, to an anionic surface active agent-containing composition results in a reduction of skin and eye damage, but surprisingly not a concomitant loss in foaming power or detergency. This discovery has provided a means of retaining the mildness of the non-ionics, and maintaining the foaming power and detergency of anionic surface active agents.

The prior art recognizes the problem of skin and eye irritation of detergent compositions such as dishwashing liquids and shampoos containing surfactants, especially the anionic surfactants, as disclosed by U.S. Pat. Nos. 4,087,518, 4,115,548, 4,195,077, 4,076,800, and British Pat. Nos. 1,478,014 and 1,529,841. All of these patents reduced the problem of the deleterious effects of detergents on the skin by adding modified proteins obtained by the chemical modification of a precursor protein, such as by the esterification or amidation of the carboxylic acid groups of the protein to obtain a highly positively charged modified protein as disclosed by U.S. Pat. No. 4,115,548; or by the acylation of the primary amino groups of the protein to obtain a highly negatively charged modified protein as disclosed by British Pat. No. 1,529,841.

U.S. Pat. No. 3,548,056 reduced the skin irritation effects of detergent compositions by the addition of a water-soluble, partially degraded protein such as peptones which may be a partially enzymatically hydrolyzed protein or a heat derived product of protein, to the surfactant-containing composition.

U.S. Pat. No. 4,140,759 reduced to the skin irritation properties of shampoos by using a lipo-protein detergent complex which is mild to the hair and scalp.

U.S. Pat. No. 3,898,186 discloses a mild liquid dishwashing composition containing a specified surface active system which includes a gel-forming gelatin, obtained by the selective hydrolysis of collagen, having a Bloom strength of 50–300 and an isoelectric point between pH 4.6 and 5.0; two anionic surfactants and an amine oxide.

Other protein-containing cosmetic compositions are disclosed in U.S. Pat. No. 3,628,974, wherein said compositions contain a gel-forming, microcrystalline, water-insoluble partial salt of collagen, formed by treating undenatured collagen with dilute acid solutions having a pH of 1.6 to 2.6; a wrinkle-decreasing aqueous solution of alpha-lactalbumin per se or in combination with beta-lactalbumin, is disclosed in U.S. Pat. No. 3,364,118; and hair spray containing an abietic acid condensate of a protein hydrolysate, is disclosed in U.S. Pat. No. 4,229,429. Crotein Q, a product of Croda Inc. of New York, is a cationic quaternary derivative of hydrolyzed collagen protein and had been used as an ingredient in hair cream rinses and other compositions containing anionic and other surface active agents.

However, none of the above cited prior art discloses a shampoo or a light duty liquid detergent composition having reduced or low skin irritation effects comprising an anionic surfactant and a minor amount of a water soluble, partially hydrolyzed, protein fraction rich in positively charged amino acids, having an isoionic point greater than 7 and a Bloom gel value of zero. The particular hydrolyzed protein fraction used herein, substantially differs from the prior art chemically-modified proteins, partially degraded proteins, lipoproteins and protein reaction products.

SUMMARY OF THE INVENTION

It has been found that a light duty liquid detergent composition comprising an anionic surfactant and a partially hydrolyzed protein fraction, rich in positively charged amino acids, having an isoionic point of 7 to 11 and a Bloom gel value of zero, counters the irritation to the skin and eyes caused by the anionic surfactant, without decreasing the foaming and detergency properties imparted to the composition by said anionic surfactant.

Accordingly, a primary object of the present invention is to provide a light duty liquid detergent having reduced or low skin irritation effects containing anionic surfactant and a partially hydrolyzed protein fraction rich in positively charged amino acids.

Another object of present invention is to provide a dishwashing liquid which is substantially non-irritating to the skin.

Still another object of the invention is to provide a shampoo composition which is substantially non-irritating to the skin and eyes.

Another object of this invention is to provide a light duty liquid detergent wherein the foaming and detergency properties of the anionic surfactant are not decreased by the presence of the water soluble partially hydrolyzed protein fraction having a high concentration of basic amino acids, and an isoionic point of 7 to 11.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel light duty liquid detergent of this invention comprises an anionic surface active agent and a positively charged, partially hydrolyzed, protein fraction containing high concentrations of basic amino acids and having an isoionic point above 7, specifically 7 to 11, and a Bloom gel value of zero, in an aqueous vehicle.

More specifically, the present invention relates to a liquid detergent composition comprising a skin irritating anionic surface active agent and about 0.2–5% of a positively charged, partially hydrolyzed, protein fraction containing high concentrations of basic amino acids obtained by extraction from a partially hydrolyzed protein mixture and isolation by ion exchange treatment with an anion exchange resin.

The novel, positively charged, protein hydrolysate fraction of the present invention which contains a high concentration of basic amino acids has an isoionic point greater than 7, a Bloom gel value of zero and a molecular weight of about 600 to 12,000, is a solid powdered material soluble in an aqueous vehicle and constitutes about 0.2 to 5%, preferably 0.7 to 1.3%, by weight of a light duty liquid detergent containing about 10–50% by weight of an anionic surfactant as the active ingredient. The positively charged protein hydrolysate fraction reduces the skin and eye irritation effects of the anionic surfactant without decreasing the foaming and detergency properties of the composition.

The positively charged, partially hydrolyzed, protein fraction having a high concentration of basic amino acids of the present invention is prepared by extraction from a hydrolyzed protein mixture and isolation of the positively charged fraction by means of ion exchange treatment with an anion exchange resin. More specifically, said protein mixture is treated with an anion exchange resin, followed by dialysis. The hydrolysate fraction may be used as such or may be optionally freeze dried to remove the water therefrom. The protein mixture may be an animal collagen hydrolysate resulting from the hydrolysis of a protein with an acid or base or enzyme. When the protein is hydrolyzed by an acid or base, it is necessary to remove the salts (NaCl) formed during said hydrolysis prior to treatment of said protein hydrolysate mixture with the anion exchange resin. The salts can be removed by dialysis of the protein hydrolysate mixture. The source of the animal collagen hydrolysate may be leather scraps, pigs feet and hooves, bones, skin or feet or pork or beef. Commercial products such as Stepan PP 37, from Stepan Chemical Co., Chicago, Illinois, an animal collagen hydrolysate from leather scraps hydrolyzed at high pH (Ca[OH]$_2$); and Lexein 100P from Inolex Corporation, Chicago, Illinois, an animal collagen hydrolysate from pigs feet and hooves, hydrolyzed by means of steam and/or acid followed by enzyme treatment, are typical collagen protein mixtures from which the novel, positively charged, protein hydrolysate fractions of present invention may be extracted and isolated.

More specifically, the process of preparing the positively charged, protein hydrolysate fraction containing a high concentration of basic amino acids of this invention comprises the steps of treating a partially hydrolyzed protein mixture with an anion exchange resin to absorb negatively charged groups from the protein onto the resin and to substitute acetate groups or other negatively charged groups from the resin therefor and dialyzing the resultant anion-exchanged, protein hydrolysate solution to remove said resin-substituted, negatively charged groups. A preferred additional first step comprises dialysis of the hydrolyzed protein mixture prior to treatment with the anion exchange resin in order to remove salts and other impurities which may be present as a result of protein hydrolysis. An optionally additional final step comprises freeze drying the positively charged protein hydrolysate fraction to remove the water therefrom and preserve it for future use. Ion exchange chromatography is a well known procedure described in the prior art. The batch phase ion exchange chromatography procedure for separation of proteins, based on charge, is described in an article by S. M. Vratsanos and I. D. Mandel entitled "Isolation of Cationic Salivary Proteins" in the *Journal of Dental Research*, Volume 56, B 109, Special Issue B, 1977. The column ion exchange chromatography method is described in a 1973 brochure by Pharmacia Fine Chemicals entitled "Sephadex ® Ion Exchangers—A Guide to Ion Exchange Chromatography". The optimal ratio of ion exchange resin to protein for fractionation of a hydrolyzed protein mixture by ion exchange chromatography is approximately 20:1. This represents the ratio of resin to protein required to just absorb the anionic proteins onto the resin, but not absorb the neutral or cationic proteins.

Any suitable anion exchange resin may be utilized in the process of producing the positively charged, protein hydrolysate fractions containing a high concentration of basic amino acids. The polystyrene- and polysaccharide-based anion exchangers are most often used. The mose important class of anion-exchange resins is based on the introduction of basic groups such as quaternary amino groups into a styrene-divinylbenzene copolymer after polymerization. These are strongly basic anion exchange resins. Examples of strong base anion exchangers are Dowex 1 and 2 resins of Dow Chemical Company; Amberlite IRA 401 and 410 resins of Rohm and Haas Company; De-Acidite FF and Duolites A-40 and A-42 of Diamond Shamrock Company; and Bio-Rad AG 1 resin of Bio-Rad Company. Weak base anion exchangers have primary or secondary amino groups attached to the polymer lattice. Commercially available weak base anion exchangers include Dowex 3, Amberlite IR-45, De-Acidite G and Duolite A-14. Cellulose anion exchangers such as diethylaminoethyl-(DEAE-) and epichlorhydrintriethanolamine (ECTEOLA-) cellulose, may also be used in the fractionation process.

The positively charged, protein hydrolysate fractions of this invention are rich in positively charged amino acids as determined by their high isoionic points of about 7 to 11; whereas, proteins presently in use commercially have isoionic points between 4 and 5. The hydrolyzed protein mixtures from which the present novel, positively charged, protein hydrolysate fractions are extracted, such as Lexein 100P and Stepan PP 37, have isoionic points of 4.8 and 4.3 respectively. The isoionic point (pI) is measured on a protein which has been thoroughly freed of all non-colloidal ions except hydrogen or hydroxide ions. It is the pH of the pure protein in distilled water. Proteins generally contain a mixture of basic amine and imine groups and acidic carboxylic groups, in the form of basic and acidic amino acids. Proteins rich in basic groups are more positively charged and exhibit high pI values; whereas, proteins rich in acidic groups will be less positively charged and exhibit low pI values. The positive charges are caused mainly by the arginine, lysine and histidine moieties. The negative charges are caused mainly by the aspartic and glutamic acid moieties. The overall charge is caused mainly by the ratio of the positively charged moieties to the negatively charged ones. Hence, a molecule rich in arginine, lysine and histidine moieties and poor in aspartic and glutamic acid moieties would have a high positive charge. For example, glycylarginine has a positively charged group and no negatively charged group, and, therefore, its positive charge is very high (pI 11). In order to obtain a protein hydrolysate fraction which contains the compound glycylarginine, the protein hydrolysate should not be dialyzed prior to being contacted with the anion exchange resin because the glycylarginine would be removed along with the inorganic salts by passing through the dialysis membrane. However, since approximately 33% of collagen is the glycine moiety, a high pI probably indicates a significant concentration of glycylarginine moieties in the positively charged ion, exchange fraction.

It has unexpectedly been found that a correlation exists between the anti-irritant properties of a glycylarginine and the positively charged protein fractions and their pI value as evidenced by Tables 1 and 2, using both in vitro and in vivo tests. The in vitro test measures the degree of curling of epidermis strips immersed in test solutions, by measuring the width of the strip at its narrowest point where curling is most pronounced. The aqueous test solutions containing 0.15% sodium linear $C_{12-14}$ alkyl benzene sulfonate (LAS) 0.10% protein are adjusted to pH 5.3 and the strips are soaked therein at room temperature for two days prior to measuring the narrowest part of the epidermis strip. The in vivo test is a skin patch test performed on guinea pigs, using 0.20% LAS and 0.10% protein is an aqueous solution.

TABLE I

| TEST MATERIAL | ISOIONIC POINT (pI) | AII* | IN VITRO (cm)** |
|---|---|---|---|
| $H_2O$ | — | 2.40 | 0.70 |
| LAS + Inolex Collagen Hydrolysate, fraction B[1] | 8.7 | 1.00 | 0.81 |
| LAS + Inolex Collagen Hydrolysate, fraction A[1] | 8.3 | 0.60 | 0.65 |
| LAS + Inolex Collagen Hydrolysate, fraction C[1] | 7.7 | — | 0.74 |
| LAS + unfractionated Inolex Collagen Hydrolysate | 4.8 | 0.20 | 0.40 |
| LAS + Inolex Collagen Hydrolysate, fraction D[2] | 3.7 | — | 0.24 |
| LAS + Inolex Collagen Hydrolysate, fraction E[2] | 3.5 | −0.60 | 0.22 |
| LAS | — | 0.00 | 0.23 |

*Guinea pig patch test anti-irritation index. The higher the score, the more effective the material (AII $Score_{LAS}$ − $Score_{LAS+Protein}$). A negative AII Score indicates the additive causes increased irritation over and above LAS.
**Half-height widths in centimeters (cm.) of test skin strips determined in in vitro epidermis curling test resulting from degrees of tissue torsion; the higher the value, the more effective the material is in preventing skin curling by detergents.
[1]A positively charged protein hydrolysate fraction obtained by an anion exchange of dialyzed Lexein 100P using BioRad AG 1 resin acetate (50–100 mesh) at a specific pH followed by neutralization to pH 7, dialysis and lyophilization. Fraction A represents the filtrate obtained at pH 10. Fraction B represents the filtrate obtained at pH 12. Fraction C represents the filtrate obtained at pH 8. Neutralizations to pH 7 were made with dilute hydrochloric acid.
[2]A negatively charged protein hydrolysate fraction obtained by anion exchange of dialyzed Lexein 100P using BioRad AG 1 resin acetate (50–100 mesh) at a specific pH. Fraction D represents the material retained by the resin at pH 2. Fraction E represents the material retained by the resin at pH 4. Materials retained by the resin were removed using 2 molar sodium chloride solution. Neutralizations to pH 7 were made with dilute sodium hydroxide.

TABLE 2

| TEST MATERIAL | ISOIONIC POINT (pI) | IN VITRO (cm)** |
|---|---|---|
| $H_2O$ | — | 0.70 |
| LAS + Glycylarginine | 11 (calc.) | 0.84 |
| LAS | — | 0.23 |

These tables clearly show decreasing epidermis curling with increasing cationicity (higher isoionic points).

Further verification of the anti-irritant activity was determined by way of primary dermal and eye irritation studies on rabbits.

TABLE 3
IN VITRO STRATUM CORNEUM CURLING TEST

| TEST MATERIAL | ISOIONIC POINT (pI) | COMPARATIVE RANKING (IN VITRO)*** |
|---|---|---|
| TEALS + Glycylarginine (dipeptide) | 11.0 | 1 |
| TEALS + Inolex Collagen Hydrolysate Fraction A | 8.3 | 2 |
| TEALS + Inolex Collagen Hydrolysate Fraction B | 8.7 | 3 |
| TEALS + Inolex Collagen Hydrolysate Fraction C | 7.7 | 4 |
| TEALS + Whole Inolex Collagen Hydrolysate Mixture | 4.8 | 5 |
| TEALS (triethanolammonium lauryl sulfate) | — | 6 |
| TEALS + Inolex Collagen Hydrolysate Fraction D | 3.7 | 7 |
| TEALS + Inolex Collagen Hydrolysate Fraction E | 3.5 | 8 |

***Test skin strips from in vitro epidermis curling test were ranked based upon the degree of curl as shown by the ratio of the narrowest width to the end width, with the strip having the least curl designated 1 and the strip with the most curl being designated 8.

TABLE 4

| TEST MATERIAL | ISOIONIC POINT (pI) | COMPARATIVE RANKING (IN VITRO)**** |
|---|---|---|
| SLS + Inolex Collagen Hydrolysate Fraction B | 8.7 | 1 |
| SLS + Inolex Collagen Hydrolysate Fraction C | 7.7 | 2 |
| SLS + Whole Inolex Collagen Hydrolysate Mixture | 4.8 | 3 |
| SLS + Inolex Collagen Hydrolysate Fraction D | 3.7 | 4 |
| SLS (sodium lauryl sulfate) | — | 5 |
| SLS + Inolex Collagen Hydrolysate Fraction E | 3.5 | 6 |

****Test skin strips from in vitro epidermis curling test were ranked based upon the degree of curl as shown by the ratio of the narrowest width to the end width, with the strip having the least curl designated 1 and strip with the most curl being designated 6.

LAS itself causes severe curling of the epidermis. When an anionic protein fraction is added to the LAS, he protein has no effect. However, when a cationic fraction is added to LAS, the protein dramatically counters the curling effect of the LAS making this strip of epidermis similar to a strip from a water treatment. Normally one would expect that positively charged proteins would interact with negatively charged detergent molecules, thereby destroying or reducing any mildness effect caused by the protein. In fact, surprisingly the mixture is mild. Although the cationic proteins neutralize the effect that LAS has on in vitro epidermis, no difference in foam height or number of dishes cleaned has been observed. Furthermore, the cationic proteins actually stabilize the foam height. There is a positive correlation between detergent induced in vivo skin irritation and in vitro epidermis curling as evidence by Table 5. A 10% solution of anionic or nonionic surfactant is used as the test solution for the in vivo test, and a 2.4% solution for the in vitro test.

TABLE 5

| DETERGENT | SKIN IRRITATION***** | CURLING RATIO** |
|---|---|---|
| SLS[1] | severe within 1 day | 0.33 |
| LAS[2] | severe within 1 day | 0.25 |
| Sodium tallow soap | intense by 4th day | 0.46 |
| AEOS - 3EO[3] | mild to moderate by 5th day | 0.96 |
| Tween 20[4] | none after 5 days | 0.92 |

**Ratio of narrow epidermis width to end width. The lower the number the more curling of the epidermis.
*****Skin irritation observed by a skilled evaluator after application of a solution containing a 10% concentration of the test composition adjusted to neutral pH to the forearm of a subject in a Duhring Chamber for a period of five days, with the solution in the Duhring Chamber being changed daily. Skin irritation observed ranges from severe reaction within one day to no reaction within five days.
[1]Sodium lauryl sulfate
[2]Sodium linear $C_{12}$–$C_{14}$ alkyl benzene sulfonate
[3]Ammonium $C_{12}$–$C_{15}$ alkyl ether triethanoxy sulfate
[4]Polyoxyethylene (20) sorbitan monolaurate Another essential ingredient of present liquid detergent compositions is the anionic surface active agent containing a sulfonate, sulfate, carboxylate or phosphate as the anionic water solubilizing group. Examples of suitable anionic detergents include the soaps, such as the water-soluble salts of higher fatty acids or rosin acids, such as may be derived from fats, oils, and waxes of animal, vegetable or marine origin, e.g., the sodium soaps of tallow, grease, coconut oil, tall oil and mixtures thereof; and the sulfated and sulfonated synthetic detergents, particularly those having about 8 to 26, and preferably about 12 to 22, carbon atoms to the molecule. Examples of suitable synthetic anionic detergents include the higher alkyl mononuclear aromatic sulfonates such as the higher alkyl benzene sulfonates containing from 8 to 16 carbon atoms in the alkyl group in a straight or branched chain, e.g. the sodium salts of decyl, undecyl, dodecyl (lauryl), tridecyl, tetradecyl, pentadecyl, or hexadecyl benzene sulfonate and the $C_8$–$C_{16}$ alkyl toluene, xylene and pheonl sulfonates: sodium $C_8$–$C_{16}$ alkyl naphthalene sulfonate, ammonium diamyl naphthalene sulfonate, and sodium dinonyl naphthalene sulfonate; sulfated aliphatic alcohols such as sodium lauryl and hexadecyl sulfates, triethanolamine lauryl sulfate, and sodium oleyl sulfate; sulfated alcohol ethers, such as lauryl, tridecyl, or tetradecyl sulfates including 1–5 ethylene oxide moieties; sulfated and sulfonated fatty oils, acids or esters, such as the sodium salts of sulfonated castor oil and sulfated red oil; sulfated hydroxyamides such as sulfated hydroxy-ethyl lauramide; sodium salt of lauryl sulfoacetate; sodium salt of dioctyl sulfosuccinate, and the sodium salt of oleyl methyl tauride.

Also included within the ambit of the invention are the sulfuric acid esters of polyhydric alcohols incompletely esterified with higher fatty acids, e.g., coconut oil monoglyceride monosulfate, tallow diglyceride monosulfate; and the hydroxy sulfonated higher fatty acid esters such as the higher fatty acid esters of low molecular weight alkylol sulfonic acids, e.g., oleic acid ester of isethionic acid.

The anionic surfactants most often used are the ammonium, mono-, di-, and triethanolamine, and alkali metal (sodium and potassium) salts of the higher alkyl benzene sulfonates, the higher alkyl sulfates, the higher fatty acid monoglyceride sulfates and the sulfated ethoxylated alcohols and mixtures thereof.

The light duty liquid detergent compositions of this invention may also contain conventional additional components such as coloring agents and perfumes; thickeners such as methyl cellulose; hydrotropic materials such as ammonium or sodium toluene or xylene sulfonate; salt; ethyl alcohol; preservatives such as formaldehyde, hydrogen peroxide, methyl, ethyl or propyl p-hydroxy benzoate; foam enhancing agents such as the amine oxides, e.g., dimethyldodecyl amine oxide, bis(2-hydroxyethyl) dodecyl amine oxide and N-dodecyl morpholine oxide, and the mono- and the di-alkylolamides of $C_{10}$–$C_{14}$ carboxylic acids such as the diethanolamide of coconut fatty acids, lauric monoethanolamide, myristic mono- 3-propanolamide, capric diethanolamide, lauric myristic mono- and di-ethanolamide. These optional additives preferably do not exceed 5% by weight of the composition.

The present light duty liquid detergents such as dishwashing liquids or shampoos are readily made by simple mixing methods.

These products have unexpectedly desirable properties when high pI proteins are added. For example, the high foam quality and cleansing performance of anionic detergents is retained but the skin and eye irritation caused by said anionics is decreased.

DETAILED DESCRIPTION OF THE INVENTION

The following examples are merely illustrative of the invention, but it is understood that the invention is not limited thereto. All amounts of various ingredients are by weight unless otherwise specified.

EXAMPLE 1

Lexein 100 P, protein hydrolysate obtained from the Inolex Corporation, is diluted to make a 5% aqueous solution. 75 ml is placed into each of ten dialysis tubes and placed into an 18 l battery jar containing distilled deionized water at 6° C. The solutions undergo equilibrium dialysis for approximately 24 hours. The dialyzed solutions may be lyophilized (freeze dried) and preserved for fractionation in the future, if desired. Dialysis removes inorganic salts and other impurities, e.g. aminoacids and peptides from the protein hydrolysate.

The dialyzed protein solutions are separated by batch phase ion exchange treatment into fractions according to charge. Six portions of 400 g of water washed Bio-Rad AG 1 resin are adjusted to pH 2, 4, 6, 8, 10 and 12 respectively with dilute HCL or dilute NaOH. Six 1000 ml samples of 2% dialyzed protein solutions are adjusted to corresponding pHs. The corresponding pH adjusted resins are added to the corresponding protein solutions, stirred for about one hour and filtered. The pH of each filtrate is adjusted to 7. The resins are each washed with a small amount of water and the washings are added to each corresponding filtrate. The pH of the combined filtrates is adjusted to 7. The resin is washed with 2 M Nacl at pH 7 until protein no longer comes off the resin. The ninhydrin test may be used to monitor this (comparison of optical density at 570 nanometers (nm) of test solution with nonexchanged protein). These NaCl washings are also adjusted to pH 7.

The filtrate solutions are equilibrium dialyzed overnight. The NaCl washings are equilibrium dialyzed for one hour periods until there is no meaningful change in the refractive index of the dialysate and then dialyzed overnight.

The contents of the dialysis bag which contains the positively charged protein fractions in an aqueous medium may be added directly to the light duty liquid detergent or may be lyophilized and added as a powder to the detergent composition such as the dishwashing formulations and shampoos in Examples 2-4.

EXAMPLE 2

Dishwashing Formulations

| INGREDIENT | PERCENT |
|---|---|
| Protein hydrolysate fraction[1] | 1.0 |
| LAS[2] | 17.0 |
| AEOS[3] | 13.0 |
| LMMEA[4] | 4.0 |
| Ethyl alcohol | 0-5 |
| SXS[5] | 0-4 |
| NaCl | 0-3 |
| Water | Q.S. |

[1] Inolex Collagen Hydrolysate Fraction A, pI - 8.3
[2] Sodium linear $C_{12}$-$C_{14}$ alkyl benzene sulfonate
[3] Ammonium salt of sulfated ethoxylated (3EO) lauryl alcohol
[4] Lauric/myristic monoethanolamide
[5] Sodium xylene sulfonate The ingredients are thoroughly admixed in an aqueous vehicle. The resulting products are clear solution exhibiting good foaming and detergency properties and substantially reduced skin irritation, i.e., essentially no erythema of the hands or arms in contact with the dishwashing liquid, in contrast to arms and hands soaked in a composition containing no protein fraction.

EXAMPLE 3

SHAMPOO

| INGREDIENT | PERCENT |
|---|---|
| Protein fraction[1] | 1 |
| Triethanolammonium lauryl sulfate | 18 |
| Cocomonoethanolamide | 3 |
| Alcohol (Ethanol) | 0-4 |
| Thickener (Hydroxypropyl methyl cellulose) | 0-4 |
| Chelating agent (EDTA)[2] | 0-1 |
| Preservative (Formalin) | 0-1 |
| Fragrance | 0-1 |
| With Water | Q.S. |

[1] Inolex Collagen Hydrolysate Fraction B - pI 8.7
[2] Ethylenediamine tetraacetic acid, tetra sodium salt

EXAMPLE 4

Shampoo

| INGREDIENT | PERCENT |
|---|---|
| Protein fraction[1] | 1 |
| Sodium lauryl sulfate | 7.5 |
| Ammonium lauryl triethanoxy ether sulfate | 2.5 |
| Lauric/Myristic Diethanolamide | 2 |
| Alcohol | 0-4 |
| Thickener | 0-4 |
| Chelating agent (EDTA sodium salt) | 0-1 |
| Preservative (Formalin) | 0-1 |
| Fragrance | 0-1 |
| With water | Q.S. |

[1] Inolex collagen hydrolysate fraction C - pI 7.7

The shampoo of Example 3 and Example 4 is prepared by thoroughly mixing the ingredients in the aqueous vehicle, resulting in clear liquid shampoo products of suitable viscosity. Results of rabbit irritation tests using the shampoo of Example 4 showed considerable reduction in eye and primary dermal irritation.

Clinical tests on shampoo products containing the positively charged protein fraction of this invention showed that test subjects using this product (exemplified by Example 4) liked this shampoo because it makes hair more manageable, leaves hair with a natural feel, improves conditioning of the hair and lathers well.

Variations in the above formulations may be made. For example, other anionic surfactants such as other higher alkyl benzene sulfonates, fatty acid soaps such as tallow soap, other sulfated alcohol ethers and the like may be substituted for the specific anionic surfactants in the examples.

Likewise, other positively charged protein hydrolysate fractions having a pI above 7 and obtained from other collagen hydrolysate sources may be substituted for the particular fraction used in the examples.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A water-soluble, partially hydrolyzed protein fraction having an isoionic point greater than 7, a Bloom gel value of zero and a molecular weight of about 600 to 12,000, obtained by extraction from a partially hydrolyzed protein mixture and isolation by ion exchange treatment with an anion exchange resin using an optimum weight ratio of resin to partially hydrolyzed protein of approximately 20:1 followed by dialysis.

2. A substantially non-irritating, liquid, detergent composition comprising an aqueous vehicle containing 10% to 50% by weight of a water-soluble, anionic surfactant and about 0.2-5% by weight of a partially hydrolyzed, protein fraction having an isoionic point greater than 7, a Bloom gel value of zero and a molecular weight of about 600 to 12,000 obtained by extraction from a partially hydrolyzed protein mixture and isolation by ion exchange treatment with an anion exchange resin followed by dialysis.

3. A liquid detergent composition according to claim 2, where said protein fraction has an isoionic point of 7 to 11.

4. A liquid detergent composition according to claim 3 wherein said anionic detergent contains a sulfonate or sulfate group in its molecular structure.

5. A liquid detergent composition according to claim 4 wherein said protein fraction is present in a concentration of 0.7% to 1.3% by weight.

6. A method of preparing the protein fraction of claim 1 which comprises the steps of (a) adjusting the pH of an aqueous partially hydrolyzed collagen protein mixture having a molecular weight of about 600 to 12,000 to the range of 8 to 12; (b) treating the mixture of step (a) with an anionic ion exchange resin using an optimum weight ratio of said resin to said mixture of approximately 20:1 in order to absorb negatively charged groups from the protein onto the resin and to substitute the negatively charged groups from said resin therefor; (c) dialyzing the mixture from step (b) to remove said resin-substituted negatively charged groups; and (d) recovering said protein fraction having a pI point greater than 7.

7. A method according to claim 6, wherein said anion exchange resin is a strongly basic anion exchange resin, said resin is maintained in a column and said treatment step (b) consists of flowing the mixture of step (a) through said column.

8. A method according to claim 7 which includes, in addition, the step of dialyzing said hydrolyzed, collagen protein mixture prior to treatment with the anion exchange resin to remove salts and other impurities.

9. A method according to claim 7, wherein step (d) consists of freeze drying said mixture from step (c).

10. A liquid detergent composition according to claim 2 wherein said ion exchange treatment employs an optimum ratio of said resin to said mixture of approximately 20:1.

* * * * *